United States Patent [19]

Pierre

[11] Patent Number: 4,857,730
[45] Date of Patent: Aug. 15, 1989

[54] APPARATUS AND METHOD FOR LOCAL CHEMICAL ANALYSES AT THE SURFACE OF SOLID MATERIALS BY SPECTROSCOPY OF X PHOTOELECTRONS

[75] Inventor: Morin Pierre, Sathonay Camp, France

[73] Assignee: Instruments S.A., France

[21] Appl. No.: 156,940

[22] PCT Filed: May 27, 1987

[86] PCT No.: PCT/FR87/00187
§ 371 Date: Jan. 27, 1988
§ 102(e) Date: Jan. 27, 1988

[87] PCT Pub. No.: WO87/07429
PCT Pub. Date: Dec. 3, 1987

[30] Foreign Application Priority Data

May 29, 1986 [FR] France .................................. 86 07740

[51] Int. Cl.⁴ .................. H01J 37/256; G01N 23/227
[52] U.S. Cl. .................................... 250/305; 250/306; 378/45; 378/143; 378/147

[58] Field of Search .................. 250/305, 306; 378/45, 378/143, 145, 147

[56] References Cited

U.S. PATENT DOCUMENTS

3,963,922  6/1976  Zulliger et al. ..................... 378/45

Primary Examiner—Jack I. Berman
Attorney, Agent, or Firm—Handal & Morofsky

[57] ABSTRACT

The apparatus for local chemical analyses at the surface of solid materials by spectroscopy of X photoelectrons comprising an ultravacuum analysis chamber 1 wherein is housed the sample to be analyzed 2 which is connected to a manipulator 3 located outside said chamber 1, an analyzer 4 in the vicinity of the sample and an electron source 5 emitting an electron beam 10 is characterized in that it comprises between the electron beam 10 and the sample 2 which is a bulky solid material, a microsource of X photons 6 placed as close as possible to said bulky sample 2.

19 Claims, 5 Drawing Sheets

APPARATUS AND METHOD FOR LOCAL CHEMICAL ANALYSES AT THE SURFACE OF SOLID MATERIALS BY SPECTROSCOPY OF X PHOTOELECTRONS

The present invention relates to an apparatus and a method for local chemical analyses at the surface of solid materials by X ray photoelectron spectroscopy.

X ray photoelectron spectroscopy (XPS) involves irradiating a sample located in an ultra high vacuum enclosure with x-ray photons photons and analyzing the photoelectrons emitted by the sample. The energy spectrum of the photoelectrons is used to discover the chemical composition of the surface as well as the nature of the chemical bonds found in the surface layers of atoms and molecules. Sources of x-ray photons include an x-ray tube of the:

type used in radiography or radiocrystallography, which is essentially composed of an anode bombarded by an electron beam, synchrotron radiation provided by some particle accelerators and the source recommended by the J. CAZAUX method from Université de REIMS wherein the sample or the sample support acts as an anode. In the CAZAUX method, one of the faces is bombarded by an electron beam and, if the sample and its support are thin enough, photoelectrons are generated on the opposite face.

Using one of the above mentioned x-ray sources typically results in an area of examination of approximately 10 mm$^2$.

Various techniques are known for reducing the area analyzed with these x-ray sources.

One technique involves collimating the x-ray source, wherein the irradiated area is reduced. However the flux of x-ray photons is correspondingly decreased and the signal-to-noise ratio of the detected signals suffers.

Another method is to reduces the analyzed area by placing a device at the analyzer input or otherwise reducing the field of observation. Once again the signal-to-noise ratio is reduced.

Reduction has been achieved by focusing the X rays with a grating. However, this reduction is also achieved at the expense of a significant loss of the signal-to-noise ratio, thus requiring the use of a multicollecting detector, When using the CAZAUX method of generating x ray photons in a thin anode a focused electron beam reduces the area, however the thin sample must be integral with the anode.

At the present time, the CAZAUX method gives the best resolution, i.e. some microns, but it only applies to thin samples, thus considerably restricting its range of application. The CAZAUX method requires samples of the order of 0,1 to 1 micron, and, it is obvious to those skilled in the art that serious problems arise with samples of such a size. First, such samples are difficult to obtain additionally, the technique of surface analysis is extremely difficult to control with such thin sample surfaces, the analyzed thickness of which may sometimes be of the order of some atomic monolayers. It is also essential to clean the sample, which of course causes problems in itself.

When X rays are to be focused by a grating, the cost of the x-ray source and the monochromator is greater than 1,000,000 francs ($165,000).

The price of a conventional x-ray source with its supply is of the order of 300,000 to 500,000 francs ($50,000 to $85,000).

The present invention provides an apparatus and a method for local chemical analyses at the surface of solid materials by X ray photoelectron spectroscopy. Furthermore, there are no strict limitations due to the sample size which may range in size greatly and analyses can be carried out on a surface, the diameter of which may vary from about 100 microns to 1 millimeter, at relatively little expense.

The apparatus of the present invention enables local chemical analyses at the surface of solid materials by X ray photoelectron spectroscopy and the simultaneous observation of the analyzed area of the sample by scanning electron microscopy. This allows for noting the presence of anomalous surface features that may affect the analysis.

More specifically, the present invention is an apparatus for local chemical analyses at the surface of solid materials by X-ray photoelectron spectroscopy that utilizes:

an ultra high vacuum analysis chamber housing the sample to be analyzed. The sample is connected to a manipulator extending, and controlled from outside the ultra vacuum chamber, An analyzer is positioned in the vicinity of the sample within the ultra high vacuum chamber and the apparatus is provided with an electron source. Between the electron source and the sample, which may be a bulky solid material, a microsource of X ray photons is provided as close as possible to the sample. The microsource consists of a body containing an anode and a collimator wherein the relationship between these components is such that the body blocks the incident electrons of the electron beam emitted by the electron source so that they are not detected after reflection on the sample. The anticathode is thick enough to stop most of the electrons of the electron beam but sufficiently thin to limit absorption of the X ray photons generated and the collimator reduces the emission angle of the photons and masks the emissive face of the anode with respect to the analyzer, as well as the inner cylinder of the collimator. Photoelectrons are emitted by the area of the sample subject to the X-ray photons and received by the analyzer.

The present invention also teaches a method for local chemical analyses at the surface of solid materials by X ray photoelectron spectroscopy.

The solid sample to be analysed, connected to a manipulator, is fitted into an ultra high vacuum analysis chamber and an analyzer is put in the vicinity of said sample.

An electron beam from an electron source, is directed towards the sample within the ultra high vacuum chamber, however:

interposed between the electron beam and the sample, as close as possible to said sample, is an X photon microsource. The X-ray photon microsource of a body containing an anticathode and a collimator, the relationship between these components is such that the body blocks the incident electrons of the electron beam so that they are not detected after reflection on the sample, the anticathode is thick enough to stop most of the electrons of the electron beam but sufficiently thin to limit absorption of the X-photons generated and the collimator reduces the emission angle of the photons and masks the emissive face of anticathode with respect to the analyzer, as well as the inner cylinder of the collimator. Photoelectrons are emitted by the sample being as a result of the impact of X-ray photons and are received by the analyzer.

The present invention also includes features that may be taken separately or in combinations.

It is preferable for the body of the X photon microsource to consist of three staged cylinders, the diameter of the first cylinder being relatively large compared with the diameter of the electron beam.

In the invention the anticathode is integral with the cylinder of smallest diameter of the body of X photon microsource and consists of a thin metal film.

The thickness of the thin metal film is in the range of 1 micron to 50 microns and the metal film is selected from a metal group consisting of aluminum, magnesium, chromium, copper and the like.

The analyzed area of the sample is to have a diameter of about 100 microns and the sample is to be inclined at an angle of about 45° to the axis of the electron beam.

The wall thickness of the body of the X photon microsource is to be above 20 microns.

The collimator is a component extending the body of the X photon microsource and may be fastened to the latter by welding or by fitting in and being held in position by friction.

The X photon microsource may be operated from outside of the ultravacuum analysis chamber by a manipulator;

The invention also contemplates focusing and scanning the electron beam, a secondary electron detector and the electronic components required for obtaining an electronic image of the microsource and the sample surface.

Various advantages and features of the present invention will be apparent from the detailed description below by reference to the accompanying drawings in which.

Figure 1:
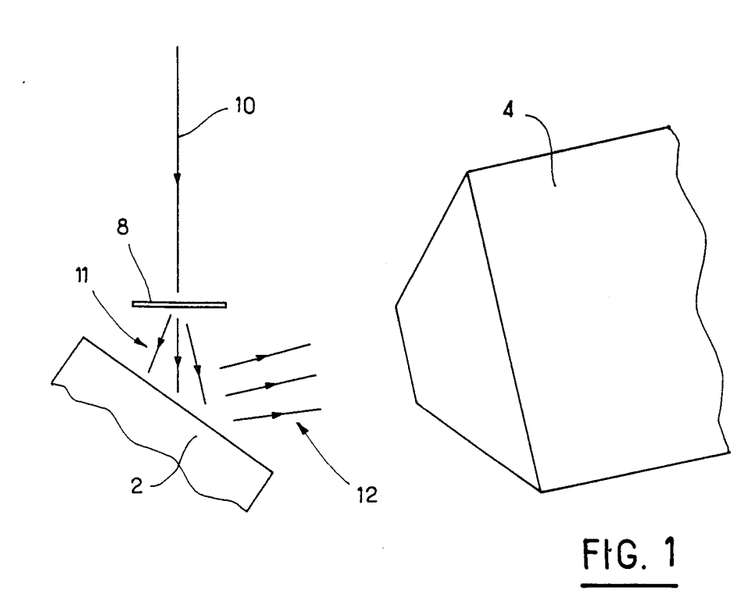
FIG. 1 is a flow sheet of the invention.
Figure 1A:
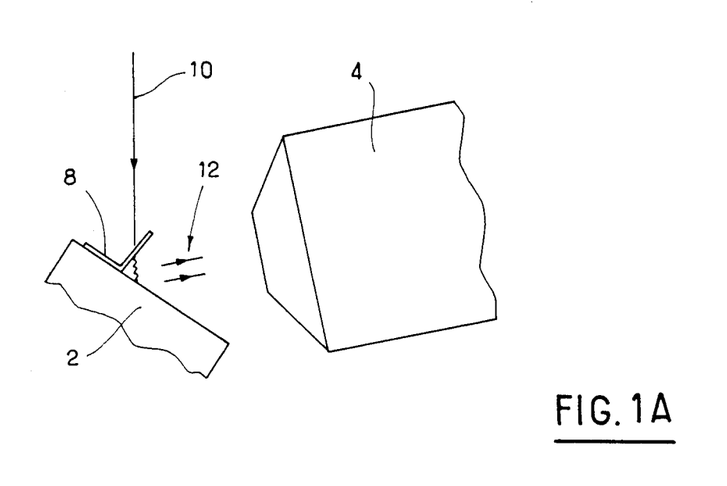
FIG. 1A illustrates a particular embodiment of the invention.
Figure 2:
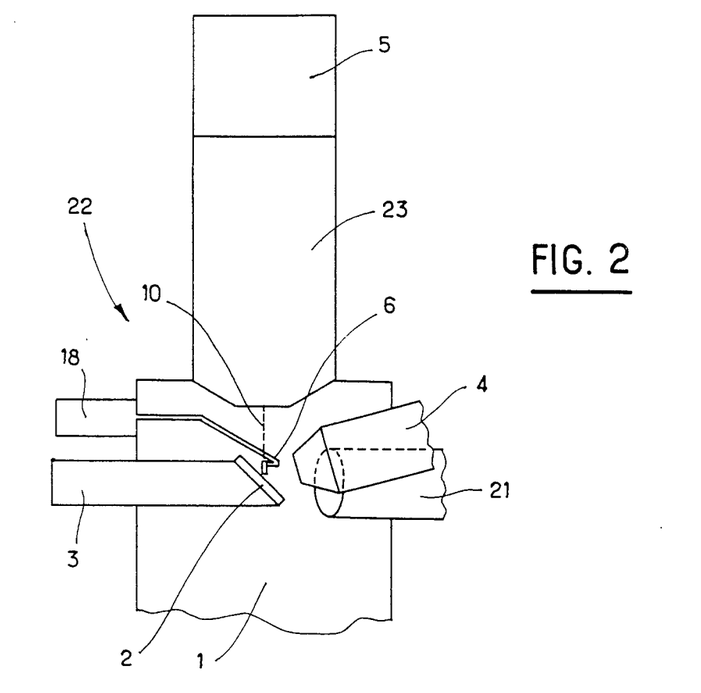
FIG. 2 illustrates a flow sheet of the apparatus according to the invention.
Figure 3:
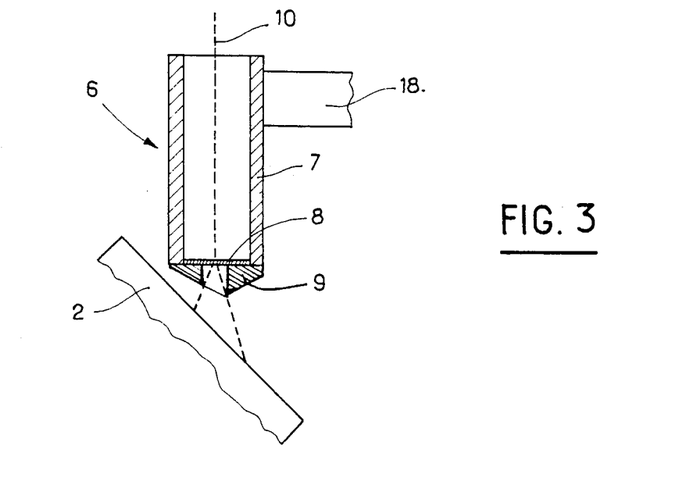
FIG. 3 shows a detail of a X photon microsource.

In the accompanying drawings where the same numerals designate similar parts, the apparatus for local chemical analyses at the surface of solid materials by X photoelectron spectroscopy is designated, as a whole, by 22 (FIG. 2).

The apparatus 22 comprises, in a known manner, an electron source 5 emitting an electron beam 10, an ultravacuum analysis chamber 1 in which is housed the sample to be analyzed 2 which is connected to a manipulator 3 located outside said chamber 1 and an analyzer 4. A microsource of X photons 6 is interposed between the electron beam 10 and the sample 2 as close as possible to said sample 2.

The X photon microsource 6 of the present invention consists of three components, a body 7, a thin metal film or anticathode 8 and a collimator 9.

The body 7 of the X photon microsource 6 comprises three staged cylinders 13, 14, 15 in order to trap the incident electrons and the electrons reemitted by the anticathode 8. The diameter of the first cylinder 13 is relatively large with respect to that of the electron beam 10 to capture the background electrons accompanying the electron beam 10. These electrons essentially result from interactions of electron beam 10 with the diaphragms of the electron source 5 or electron gun. The general shape resulting from these staged cylinders 13, 14, 15 allows to come close to the surface of a sample 2 inclined at an angle of about 45°.

X photons are generated in the metal film or anticathode 8. The materials used are those generally used for making anticathodes, that is, aluminum, magnesium, chromium, copper and similar metals. The thickness of the metal film 8 should be such that all incident electrons are stopped, but it should be the smallest possible in order to minimise absorption of the X photons before exiting the anticathode 8. For instance, a thin aluminum film of 3 microns is suitable for an electron beam 10 of 15 kV. Concerning the thin film, the size can be varied in the range of 1 to 50 microns. The structure of the anticathode 8 according to the present invention assures, on one hand a sufficient photon flux, on the other hand that the emissive surface, that is the end part, is not facing the analyzer; as a matter of fact, it is essential that the anticathode 8 should be as close as possible to the sample 2 and is situated in order not to mask the analyzed area with respect to analyzer 4; thus, the closer is the anticathode 8 to the sample 2, the smaller is the surface to be analyzed.

The collimator 9 is the third component of the X photoelectron microsource 6 of the apparatus according to the invention. The primary function of the collimator 9 is to reduce the irradiated surface of sample 2 in order to improve the spatial analysis resolution. The electron beam 10 being focused at centre of the anticathode 8 (point 0, FIGS. 6 and 7), the irradiated surface 19 of sample 2 is then defined by the closed curve A F B E A (FIG. 7) obtained by drawing straight lines from point 0 and passing through the lower end of the collimator 9 (in case the electron beam 10 is not strictly ponctual, the irradiated surface 19 will be slightly superior to that previously defined. The broadening due to this effect can be inferior to a 10% increase of the irradiated surface).

Figure 6:
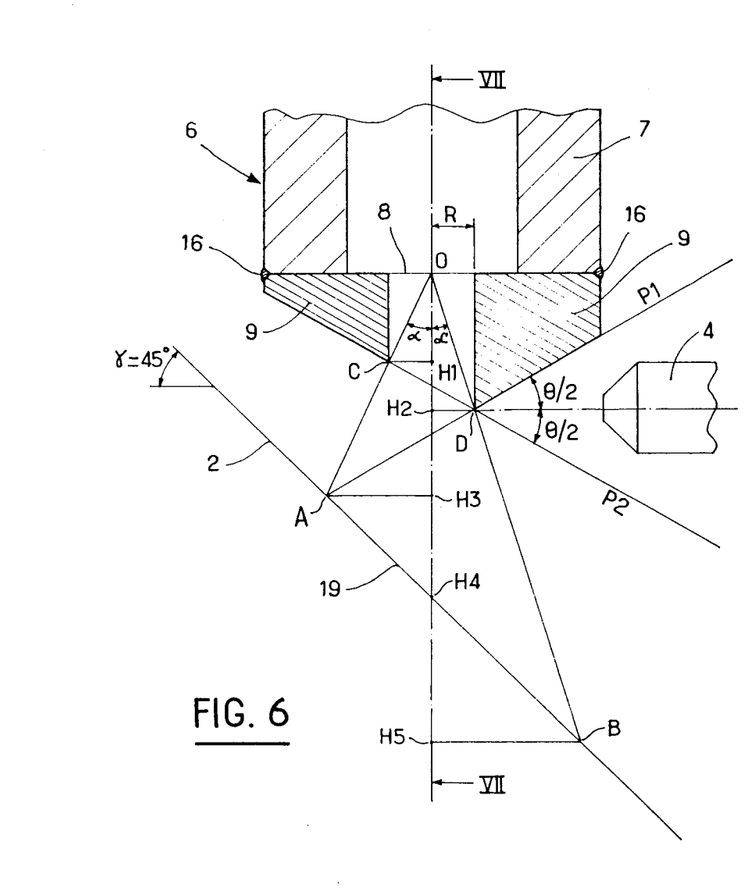
FIG. 6 is a cross-sectional view taken on line VII—VII of FIG. 7.

The end part of the collimator 9 has been designed in such a way that, on one hand the collimator 9 does not mask, towards the analyzer 4, the irradiated surface 19 of sample 2, on the other hand the inner cylinder of collimator 9 and the anticathode 8 are not facing analyzer 4. As a matter of fact, these components being irradiated by X photons, they emit photoelectrons 12; a background signal would result if they were detected by analyzer 4. Therefore, the collimator 9 ends in two inclined planes $P_1$ and $P_2$ (FIG. 6) tangent to the "acceptance" cone of analyzer 4, the positions of which can be determined as follows:

Let us consider the case the electron beam 10 is vertical, the analyzer axis 4 is horizontal and the sample 2 is inclined at 45° (FIG. 6). The radius R of collimator 9 is selected on grounds of mechanical feasibility and the angle alpha is determined on grounds of X photon beam 11 intensity. Both parameters R and alpha set the position of point C. The plane $P_2$ inclined at an angle of $-(\theta/2)$ with respect to the horizontal is drawn through the point C, $\theta/2$ is the half-angle of "acceptance" of analyzer 4. The intersection of that plane with cylinder 2R gives the point D. A plane set at an angle of $(\theta/2)$ with respect to the horizontal is drawn through the point D, intersection of this plane with the straight line OC gives the point A. The point A being a point of sample 2, the position of the sample with respect to the X photon microsource 6 will therefore be set. The following values can be inferred from above mentioned construction:

(1) Position of point $C$ $OH_1 = \dfrac{R}{tg\alpha}$ (2) Position of point $D$ $OH_2 = \dfrac{R}{tg\alpha} + 2R tg \dfrac{\theta}{2}$ (3) Distance anticathode (8) − sample (2)

$$OH_4 = R\left(1 + \dfrac{1}{tg\alpha}\right) \dfrac{1 + 3\, tg\alpha\, tg \dfrac{\theta}{2}}{1 - tg\alpha\, tg \dfrac{\theta}{2}}$$

(4) Size of the irradiated surface (19) of sample (2)

$$AB = 2R \dfrac{1 + tg\alpha\, tg \dfrac{\theta}{2}}{1 - tg\alpha\, tg \dfrac{\theta}{2}} \times \dfrac{1 + 3\, tg\alpha\, tg \dfrac{\theta}{2}}{1 - tg\alpha + 2\, tg\alpha\, tg \dfrac{\theta}{2}}$$

$$EF = 2R(1 + tg\alpha) \dfrac{1 + 3\, tg\alpha\, tg \dfrac{\theta}{2}}{1 - tg^2\alpha\, tg^2 \dfrac{\theta}{2}}$$

Figure 7:
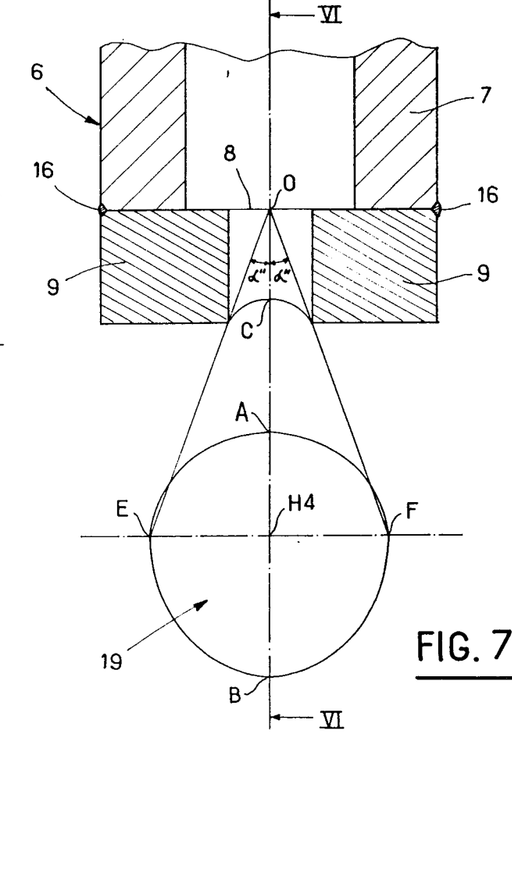
FIG. 7 is a cross-sectional view taken on line VI—VI of FIG. 6.

Thus, according to the geometry illustrated in the FIGS. 6 and 7 and with the values R=25 microns, $\alpha=25°$, $\theta/2=30°$, one obtains the values hereinafter: $OH_1=53$ microns, $OH_2=82$ microns, $OH_4=200$ microns, AB=200 microns and EF=150 microns.

Figure 4:
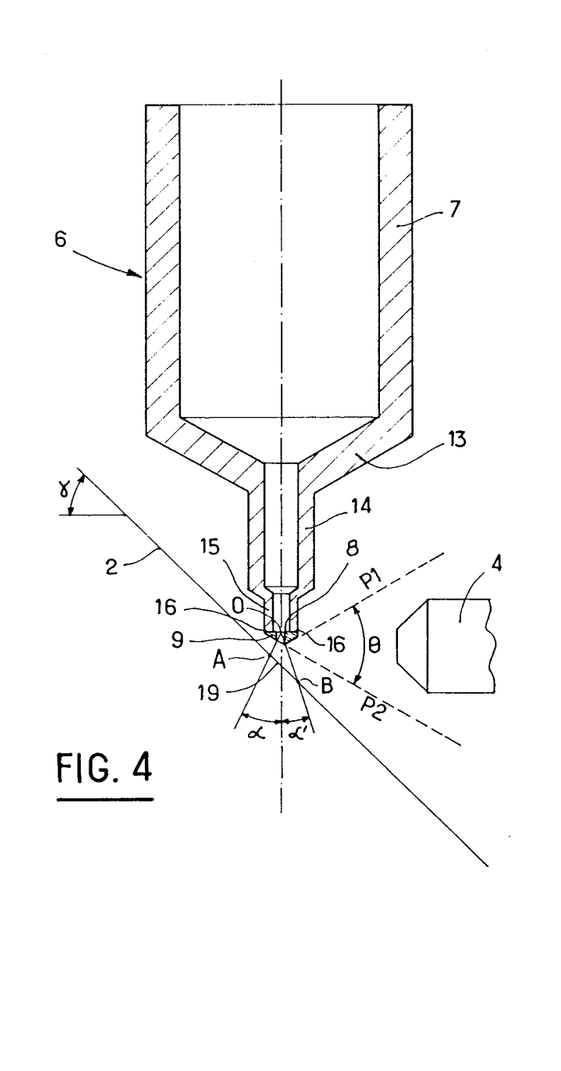
FIG. 4 illustrates a first embodiment of a X photon microsource according to the invention.
Figure 5:
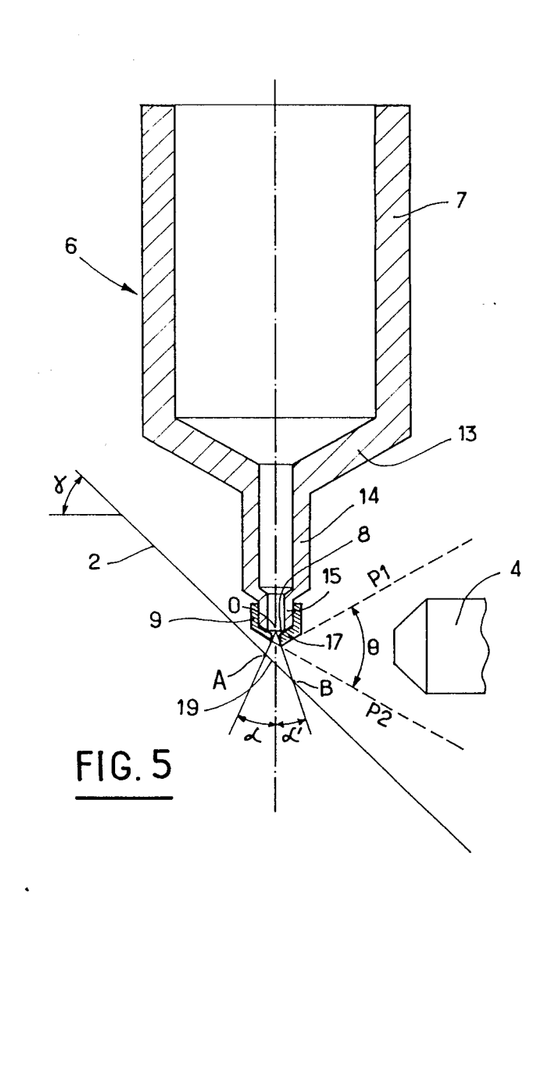
FIG. 5 illustrates a second embodiment of a X photon microsource according to the invention.

In the X photon microsource 6 of the invention, the collimator 9 is a component extending the body 7 which is fastened to the latter by any appropriate means. By way of example, the collimator 9 is welded to the body 7 as indicated at 16 or is fastened by fitting in as indicated at 17 in the FIGS. 4 and 5. The effect of the body 7 of X photon microsource 6 is to block the incident electrons so that they are not detected after reflection on sample 2. The walls of the body 7 must be sufficiently thick and have a thickness above 20 microns in order to stop the photons emitted towards the walls of body 7.

The X photo microsource 6 is operated by a manipulator 18. The manipulator 18 permits displacement of the anticathode 8 which is inside the ultravacuum chamber 1. The link between the manipulator 18 and the anticathode 8 provides electrical insulation of the anticathode 6 and informs about the intensity of the electron beam 10 and therefore about of the intensity of X photon beam. In the prior art, it has already been suggested to put a X ray source in an ultravacuum enclosure but, in this case, the anticathode is bulky and must be located very remote from sample. Because the source is very remote from the sample, a very high power, generally of the order of 150 watts is needed, which involves cooling of the anticathode by a fluid. As a result, the irradiated surface of the sample is of the order of 10 mm² and a local analysis cannot be obtained.

One of the features of the present invention lies in that the sample size is not limited and may have any value. Furthermore, the local analysis achieved with the apparatus and the method according to the present invention ensures an analysis range of sample in the range of 100 microns which cannot presently be obtained with the prior art devices when bulky solid materials are used. With the prior art devices, this analysis range requires a focusing system of X rays.

Figure 8:
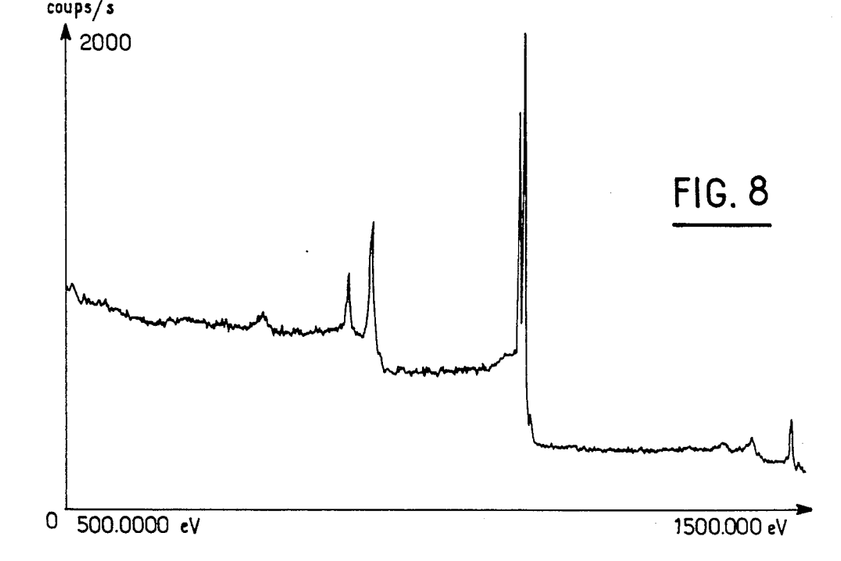
FIGS. 8 and 8 illustrate experimental results; on these figures, the photoelectron energy in electron-volts is plotted as abscissa and the counts per second as ordinate.
Figure 9:
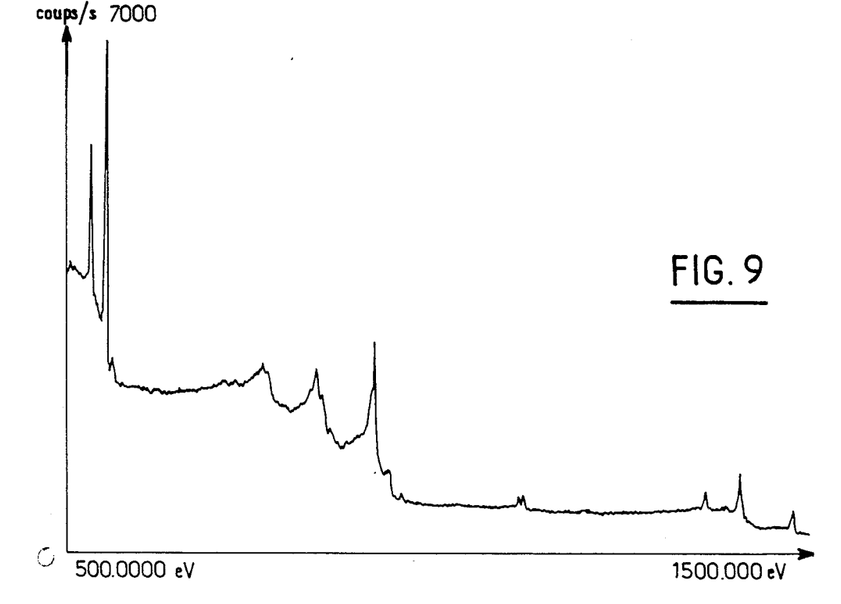

The FIGS. 8 and 9 show the spectra of a sample of silver and copper with a beam energy of 40 KeV and an intensity of 0.7 $\mu$A, the energy width of the analyzer window being 3 eV, the data collecting time for the copper spectrum is 3 hours and that of the silver 1½ hours.

The counting rate corresponding to the highest peak of the copper spectrum equals 7000 c/s. From this result, it can be seen that the counting rate is 10 times higher than that given by a conventional X source collimated on 1 mm². By means of the apparatus and the method according to the present invention, one obtains on a surface of 100 microns diameter a counting rate equivalent to that obtained on a surface of 10 mm diameter with a conventional X source according to the prior art.

Therefore, those skilled in the art will appreciate the significant advantages gained in practising the present invention such as the:

a moderate price of the apparatus and the ability to use a specimen which is not limited as to its size.

Other advantages include the ability to analyze a surface area on the order of 100 microns diameter and the ability to localize the analysis by scanning electron microscopy.

The invention is not limited to the embodiment shown and described in more details and various modifications can be made without departing from its scope.

I claim:

1. Apparatus for local chemical analyses at a surface of a solid material by X-ray photoelectron spectroscopy, comprising:
   (a) an ultra high vacuum analysis chamber for housing a sample to be analyzed;
   (b) support means for supporting said sample, said support means extending outside said chamber;
   (c) an analyzer positioned within said ultra high vacuum analysis chamber in the vicinity of the sample;
   (d) an electron source capable of emitting an electron beam; and
   (e) a microsource of X-ray photons positioned between said electron source and said sample along the path of said electron beam provided as close as possible to said solid sample, comprising:
   (i) a body comprising three staged cylinders, the diameter of the first cylinder being relatively large compared with that of the electron beam;
   (ii) an anode contained within said body; and
   (iii) a collimator, wherein said body blocks incident electrons of said electron beam so that said electrons are not detected after reflection on said sample, said anode being thick enough to stop most of the electrons of said electron beam but sufficiently thin to limit absorption of X-ray photons generated and said collimator reduces an emission angle of the photons and masks an emissive face of said anode with respect to the analyzer, as well as an inner cylinder of the colimator, photoelectrons being emitted by the sample being received by said analyzer.

2. Apparatus either of claims 1, wherein the anticathode (8) is integral with the cylinder of smallest diameter (15) of the body (7) of the microsource of X photons (6) and consists of a thin metal film.

3. Apparatus as claimed in claim 1 wherein the thickness of the thin metal film (8) is in the range of 1 micron to 50 microns.

4. Apparatus as claimed in claim 1 wherein the metal film (8) is selected from a metal group consisting of aluminum, magnesium chromium and copper.

5. Apparatus as claimed in claim 4, wherein the metal film is a metal selected from a group comprising aluminum, magnesium and chromium.

6. Apparatus as claimed in claim 1, wherein the analyzed area of sample (2) has a diameter (19) of about 100 microns.

7. Apparatus as claimed in claim 1, wherein the sample (2) is inclined at an angle of about 45°.

8. Apparatus as claimed in claim 1, wherein the wall thickness of the body (7) of the microsource of X photons (6) is above 20 microns.

9. Apparatus as claimed in claim 1, wherein the collimator (9) is a component extending the body (7) of the microsource of X photons (6) which is fastened to the latter by welding (16).

10. Apparatus as claimed in claim 1, wherein the collimator (9) is a component extending the body (7) of the microsource of X photons (6) which is fastened to the latter by fitting in (17).

11. Apparatus as claimed in claim 1, wherein the microsource of X photons (6) is operated from outside of the ultravacuum analysis chamber (1) by a manipulator (18).

12. Apparatus as claimed in claim 1, wherein it comprises a device (23) for focusing and scanning the electron beam (10), a secondary electron detector (21) and the electronic components required for obtaining an electronic image of the microsource (6) and the surface of sample (2).

13. Apparatus as claimed in claim 1, wherein the collimator end nearest the sample comprises two surfaces defining an angle having an adjacent supplementary angle $\theta$ said angle $\theta$ bisected by the an axis on which said analyzer is aligned.

14. Method for local chemical analyses at a surface of solid materials by spectroscopy of X-ray photoelectrons, wherein:
(a) a solid sample to be analyzed, connected to a manipulator is fitted into an ultravacuum analysis chamber;
(b) an analyzer is placed within the ultra high vacuum analysis chamber in the vicinity of said sample;
(c) scanning the sample with an electron beam from an electron source and
(d) interposing between the electron beam and the sample, as close as possible to said sample, a microsource of X-ray photons comprising a body containing an anode and a collimator such that the body blocks the incident electrons of the electron beam so that they are not detected after reflection on the sample, the anode thick enough to stop most of the electrons of said electron beam but sufficiently thin to limit absorption of X-ray photons generated and the collimator reducing an emission angle of the photons and masking an emissive face of said anode with respect to the analyzer, as well as an inner cylinder of the collimator, photoelectrons emitted by the sample being received by said analyzer.

15. Apparatus for local analysis of a surface of a solid material by X-ray photoelectron spectroscopy, comprising:
(a) an ultra high vacuum analysis chamber;
(b) a first support for holding a sample within said ultra high vacuum analysis chamber;
(c) an electron source for introducing an electron beam into said ultra high vacuum analysis chamber;
(d) a focusing means for focusing said electron beam;
(e) a microsource of X-ray photons, positioned between said electron source and said sample along the path of said electron beam, comprising:
(i) a three staged, cylindrical body;
(ii) an anode, integral with said body, of metal film, and
(iii) a collimator with angled faces at an output end;
(f) a second support for orienting said microsource within said ultravacuum analysis chamber; and
(g) a device for receiving photoelectron emissions of said sample, said device in close proximity to said sample within said ultra high vacuum analysis chamber.

16. An apparatus as claimed in claim 15, wherein said anode is of a thickness within the range of 1 to 50 microns and the metal is selected from a group consisting of aluminum, magnesium and chromium.

17. An apparatus as claimed in claim 15 further comprising a secondary electron detector to enable electronic imaging of said microsource and said sample.

18. An apparatus as claimed in claim 15, wherein said sample is positioned so the surface analyzed is at a 45° angle with respect to said electron beam.

19. An apparatus as claimed in claim 18, wherein said device for receiving photoelectron emissions is aligned on an axis that bisects an adjacent supplementary angle to an angle defined by said angled faces of the output end of said collimator.

* * * * *

UNITED STATES PATENT AND TRADEMARK OFFICE
CERTIFICATE OF CORRECTION

PATENT NO. : 4,857,730

DATED : August 15, 1989

INVENTOR(S) : MORIN

It is certified that error appears in the above-identified patent and that said Letters Patent is hereby corrected as shown below:

Title page:

(75) Inventor: Pierre Morin, Sathonay Camp, France

Item [19] "Pierre" should read --Morin--

Signed and Sealed this

Sixteenth Day of October, 1990

Attest:

HARRY F. MANBECK, JR.

*Attesting Officer*  *Commissioner of Patents and Trademarks*